United States Patent
Kohara et al.

(10) Patent No.: US 8,466,273 B2
(45) Date of Patent: Jun. 18, 2013

(54) HEPATITIS C VIRUS INHIBITORS

(75) Inventors: Kyoko Kohara, Kumamoto (JP); Michinori Kohara, Tokyo (JP); Tomohiro Nishimura, Kikuchi (JP); Masaaki Sato, Kumamoto (JP)

(73) Assignees: Juridical Foundation The Chemo-Sero-Therapeutic Research Institute, Kumamoto (JP); Tokyo Metropolitan Institute of Medical Science, Tokyo (JP); National University Corporation Kumamoto University, Kumamoto (JP)

( * ) Notice: Subject to any disclaimer, the term of this patent is extended or adjusted under 35 U.S.C. 154(b) by 372 days.

(21) Appl. No.: 12/241,868

(22) Filed: Sep. 30, 2008

(65) Prior Publication Data

US 2009/0234102 A1    Sep. 17, 2009

(30) Foreign Application Priority Data

Mar. 14, 2008   (JP) .................. 2008-066158

(51) Int. Cl.
*C07H 21/04*    (2006.01)
(52) U.S. Cl.
USPC .......... 536/24.5; 536/24.31; 536/24.1; 435/6; 435/325; 435/375; 514/44

(58) Field of Classification Search
None
See application file for complete search history.

(56) References Cited

U.S. PATENT DOCUMENTS

| 5,712,148 A * | 1/1998 | Borden et al. ................. 435/356 |
| 7,510,851 B2 * | 3/2009 | Waters et al. .................... 435/25 |
| 2003/0143732 A1 * | 7/2003 | Fosnaugh et al. ............. 435/325 |
| 2007/0141009 A1 * | 6/2007 | Khan ......................... 424/70.13 |

FOREIGN PATENT DOCUMENTS

| EP | 1 090 996 A1 | 4/2001 |
| WO | WO 99/67394 A1 | 12/1999 |

OTHER PUBLICATIONS

Choo et al., "Isolation of a cDNA Clone Derived from a Blood-Borne Non-A, Non-B Viral Hepatitis Genome," Science, 1989, 244:359-362.
Ji et al., "Selective Loss of AKR1C1 and AKR1C2 in Breast Cancer and Their Potential Effect on Progesterone Signaling," Caner Research, Oct. 15, 2004, 64:7610-7617.
Kato et al., "Molecular cloning of the human hepatitis C virus genome from Japanese patients with non-A, non-B hepatitis," Proc. Natl. Acad. Sci. USA, Dec. 1990, 87:9524-9528.
Steckelbroeck et al., "Tibolone Meatbolism in Human Liver is Catalyzed by 3α/3β-Hydroxysteroid Dehydrogenase Activities of the Four Isoforms of the Aldo-Keto Reductase (AKR)1C Subfamily," J. Pharm. Exp. Ther., 2006, 316:1300-1309.
Yamauchi et al., "Cloning of a Na+- and Cl--dependent Betaine Transporter That is Regulated by Hypertonicity," J. Biol. Chem.., Jan. 5, 1992, 267(1):649-652.
Zheng et al., "Gene Expression Profiles of HeLa Cells Impacted by Hepatitis C Virus Non-structural Protein NS4B," J. Biochem. Mol. Biol., Mar. 2005, 38(2):151-160.

* cited by examiner

*Primary Examiner* — Kimberly Chong
(74) *Attorney, Agent, or Firm* — Foley & Lardner LLP

(57) ABSTRACT

The present invention aims to provide hepatitis C virus inhibitors capable of inhibiting viral replication in hepatitis C virus-infected cells.

The replication of hepatitis C virus can be inhibited and hepatitis C virus-infected cells can be specifically injured by specifically inhibiting BGT-1 or AKR1C1 involved in the replication of hepatitis C virus. Thus, viral inhibitors comprising a substance inhibiting BGT-1 or AKR1C1 are effective for the treatment of hepatitis C.

6 Claims, 8 Drawing Sheets

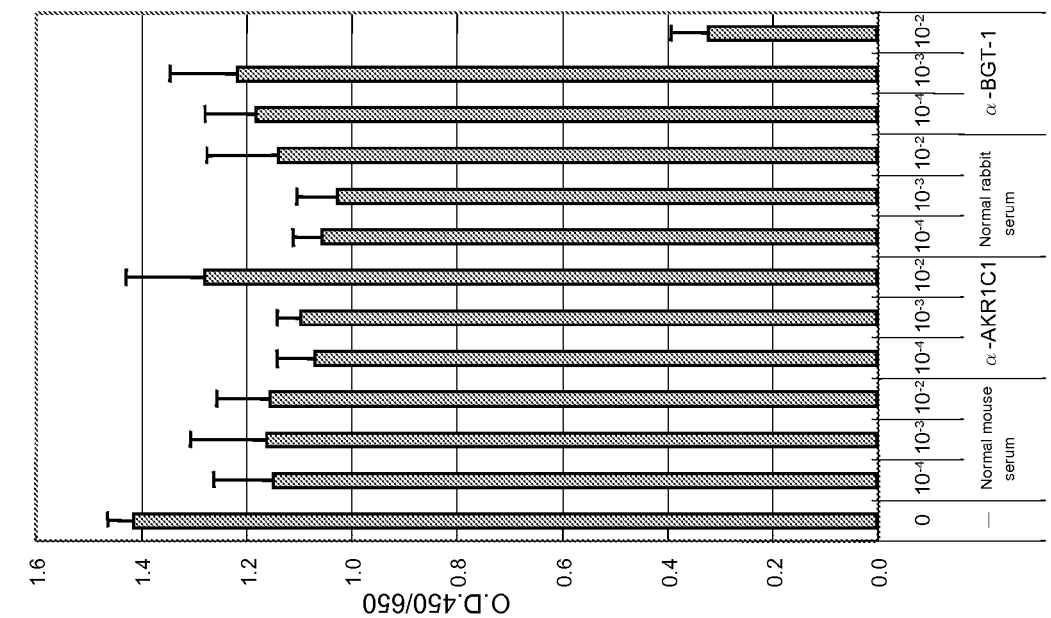
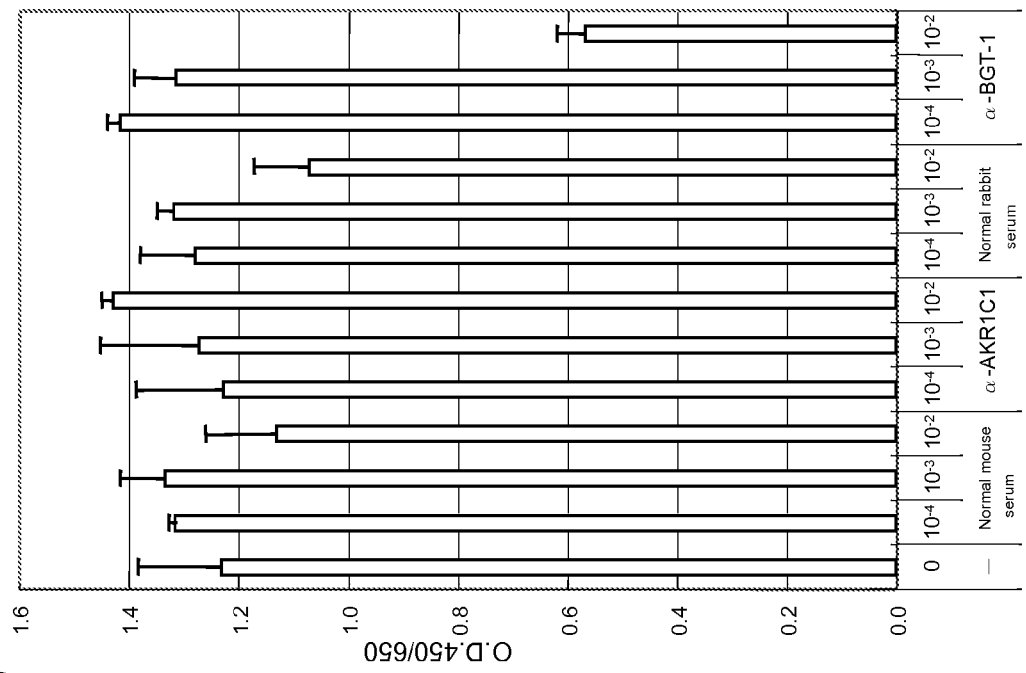
Figure 5

SEQUENCE LISTING

```
<160> NUMBER OF SEQ ID NOS: 35

<210> SEQ ID NO 1
<211> LENGTH: 25
<212> TYPE: RNA
<213> ORGANISM: Artificial
<220> FEATURE:
<223> OTHER INFORMATION: siRNA for BGT-1 (120-144)

<400> SEQUENCE: 1
caacaagaug gaguuugugc uguca                                          25

<210> SEQ ID NO 2
<211> LENGTH: 25
<212> TYPE: RNA
<213> ORGANISM: Artificial
<220> FEATURE:
<223> OTHER INFORMATION: siRNA for BGT-1 (362-386)

<400> SEQUENCE: 2
caucuguggu caucgaguca uauuu                                          25

<210> SEQ ID NO 3
<211> LENGTH: 25
<212> TYPE: RNA
<213> ORGANISM: Artificial
<220> FEATURE:
<223> OTHER INFORMATION: siRNA for BGT-1 (488-512)

<400> SEQUENCE: 3
cagagcauug cacggacuuu cugaa                                          25

<210> SEQ ID NO 4
<211> LENGTH: 25
<212> TYPE: RNA
<213> ORGANISM: Artificial
<220> FEATURE:
<223> OTHER INFORMATION: siRNA for BGT-1 (711-735)

<400> SEQUENCE: 4
ggugguuuau uucacagcca cguuu                                          25

<210> SEQ ID NO 5
<211> LENGTH: 25
<212> TYPE: RNA
<213> ORGANISM: Artificial
<220> FEATURE:
<223> OTHER INFORMATION: siRNA for BGT-1 (728-752)

<400> SEQUENCE: 5
ccacguuucc guaccugaug cuugu                                          25

<210> SEQ ID NO 6
<211> LENGTH: 25
<212> TYPE: RNA
```

```
<213> ORGANISM: Artificial
<220> FEATURE:
<223> OTHER INFORMATION: siRNA for BGT-1 (801-825)

<400> SEQUENCE: 6
caucuacuac uugaagccag auuug                                      25

<210> SEQ ID NO 7
<211> LENGTH: 25
<212> TYPE: RNA
<213> ORGANISM: Artificial
<220> FEATURE:
<223> OTHER INFORMATION: siRNA for BGT-1 (1133-1157)

<400> SEQUENCE: 7
agcugggguc cugccuguuc uuuau                                      25

<210> SEQ ID NO 8
<211> LENGTH: 25
<212> TYPE: RNA
<213> ORGANISM: Artificial
<220> FEATURE:
<223> OTHER INFORMATION: siRNA for BGT-1 (1144-1168)

<400> SEQUENCE: 8
ugccuguucu uuaucaugcu cauau                                      25

<210> SEQ ID NO 9
<211> LENGTH: 25
<212> TYPE: RNA
<213> ORGANISM: Artificial
<220> FEATURE:
<223> OTHER INFORMATION: siRNA for BGT-1 (1145-1169)

<400> SEQUENCE: 9
gccuguucuu uaucaugcuc auauu                                      25

<210> SEQ ID NO 10
<211> LENGTH: 25
<212> TYPE: RNA
<213> ORGANISM: Artificial
<220> FEATURE:
<223> OTHER INFORMATION: siRNA for BGT-1 (1568-1592)

<400> SEQUENCE: 10
ucaaguacaa caacgucuau gugua                                      25

<210> SEQ ID NO 11
<211> LENGTH: 32
<212> TYPE: RNA
<213> ORGANISM: Artificial
<220> FEATURE:
<223> OTHER INFORMATION: siRNA for AKR1C1 (2-33)

<400> SEQUENCE: 11
uggauucgaa auaucagugu gugaagcuga au                              32

<210> SEQ ID NO 12
<211> LENGTH: 25
<212> TYPE: RNA
<213> ORGANISM: Artificial
<220> FEATURE:
<223> OTHER INFORMATION: siRNA for AKR1C1 (8-32)

<400> SEQUENCE: 12
cgaaauauca gugugugaag cugaa                                      25
```

```
<210> SEQ ID NO 13
<211> LENGTH: 25
<212> TYPE: RNA
<213> ORGANISM: Artificial
<220> FEATURE:
<223> OTHER INFORMATION: siRNA for AKR1C1 (93-117)

<400> SEQUENCE: 13
aaguaaagcu uuagaggcca ccaaa                                               25

<210> SEQ ID NO 14
<211> LENGTH: 25
<212> TYPE: RNA
<213> ORGANISM: Artificial
<220> FEATURE:
<223> OTHER INFORMATION: siRNA for AKR1C1 (94-118)

<400> SEQUENCE: 14
aguaaagcuu uagaggccac caaau                                               25

<210> SEQ ID NO 15
<211> LENGTH: 25
<212> TYPE: RNA
<213> ORGANISM: Artificial
<220> FEATURE:
<223> OTHER INFORMATION: siRNA for AKR1C1 (105-129)

<400> SEQUENCE: 15
agaggccacc aaauuggcaa uugaa                                               25

<210> SEQ ID NO 16
<211> LENGTH: 25
<212> TYPE: RNA
<213> ORGANISM: Artificial
<220> FEATURE:
<223> OTHER INFORMATION: siRNA for AKR1C1 (121-145)

<400> SEQUENCE: 16
gcaauugaag cuggcuuccg ccaua                                               25

<210> SEQ ID NO 17
<211> LENGTH: 25
<212> TYPE: RNA
<213> ORGANISM: Artificial
<220> FEATURE:
<223> OTHER INFORMATION: siRNA for AKR1C1 (138-162)

<400> SEQUENCE: 17
ccgccauauu gauucugcuc auuua                                               25

<210> SEQ ID NO 18
<211> LENGTH: 25
<212> TYPE: RNA
<213> ORGANISM: Artificial
<220> FEATURE:
<223> OTHER INFORMATION: siRNA for AKR1C1 (323-347)

<400> SEQUENCE: 18
uggauuaugu ugaccucuac cuuau                                               25

<210> SEQ ID NO 19
<211> LENGTH: 25
<212> TYPE: RNA
<213> ORGANISM: Artificial
<220> FEATURE:
<223> OTHER INFORMATION: siRNA for AKR1C1 (558-582)
```

```
<400> SEQUENCE: 19
ugucugcaac cagguggaau gucau                                              25

<210> SEQ ID NO 20
<211> LENGTH: 25
<212> TYPE: RNA
<213> ORGANISM: Artificial
<220> FEATURE:
<223> OTHER INFORMATION: siRNA for AKR1C1 (827-851)

<400> SEQUENCE: 20
gcaucagaca gaacgugcag guguu                                              25

<210> SEQ ID NO 21
<211> LENGTH: 25
<212> TYPE: RNA
<213> ORGANISM: Artificial
<220> FEATURE:
<223> OTHER INFORMATION: siRNA for AKR1C1 (893-917)

<400> SEQUENCE: 21
gccuaaacag aaaugugcga uauuu                                              25

<210> SEQ ID NO 22
<211> LENGTH: 80
<212> TYPE: DNA
<213> ORGANISM: Artificial
<220> FEATURE:
<223> OTHER INFORMATION: Region of AKR1C1 (91-170)

<400> SEQUENCE: 22
aaaagtaaag ctttagaggc caccaaattg gcaattgaag ctggcttccg ccatattgat        60
tctgctcatt tatacaataa                                                    80

<210> SEQ ID NO 23
<211> LENGTH: 25
<212> TYPE: RNA
<213> ORGANISM: Artificial
<220> FEATURE:
<223> OTHER INFORMATION: Control siRNA for BGT-1

<400> SEQUENCE: 23
caaagagguu gaguucgugu cauca                                              25

<210> SEQ ID NO 24
<211> LENGTH: 25
<212> TYPE: RNA
<213> ORGANISM: Artificial
<220> FEATURE:
<223> OTHER INFORMATION: Control siRNA for AKR1C1

<400> SEQUENCE: 24
aagaacguua uagggcccac auaaa                                              25

<210> SEQ ID NO 25
<211> LENGTH: 21
<212> TYPE: RNA
<213> ORGANISM: Artificial
<220> FEATURE:
<223> OTHER INFORMATION: siRNA for p53m2

<400> SEQUENCE: 25
gacuccagug auaaucugcu u                                                  21

<210> SEQ ID NO 26
```

```
<211> LENGTH: 22
<212> TYPE: RNA
<213> ORGANISM: Artificial
<220> FEATURE:
<223> OTHER INFORMATION: siRNA for HCV (R5)

<400> SEQUENCE: 26
gucucguaga ccgugcauca uu                                                  22

<210> SEQ ID NO 27
<211> LENGTH: 22
<212> TYPE: DNA
<213> ORGANISM: Artificial
<220> FEATURE:
<223> OTHER INFORMATION: siRNA for HCV (R7)

<400> SEQUENCE: 27
gucucguaga ccgugcacca tt                                                  22

<210> SEQ ID NO 28
<211> LENGTH: 21
<212> TYPE: RNA
<213> ORGANISM: Artificial
<220> FEATURE:
<223> OTHER INFORMATION: siRNA for DHCR24_417 (417-435)

<400> SEQUENCE: 28
guacaagaag acacacaaau u                                                   21

<210> SEQ ID NO 29
<211> LENGTH: 21
<212> TYPE: RNA
<213> ORGANISM: Artificial
<220> FEATURE:
<223> OTHER INFORMATION: siRNA for DHCR24_1024 (1024-1042)

<400> SEQUENCE: 29
gagaacuauc ugaagacaau u                                                   21

<210> SEQ ID NO 30
<211> LENGTH: 25
<212> TYPE: DNA
<213> ORGANISM: Artificial
<220> FEATURE:
<223> OTHER INFORMATION: Forward primer for BGT-1

<400> SEQUENCE: 30
aagaacgtta tagggcccac ataaa                                               25

<210> SEQ ID NO 31
<211> LENGTH: 27
<212> TYPE: DNA
<213> ORGANISM: Artificial
<220> FEATURE:
<223> OTHER INFORMATION: Reverse primer for BGT-1

<400> SEQUENCE: 31
caaatgggtc tccttctccc cggctat                                             27

<210> SEQ ID NO 32
<211> LENGTH: 27
<212> TYPE: DNA
<213> ORGANISM: Artificial
<220> FEATURE:
<223> OTHER INFORMATION: Forward primer for AKR1C1

<400> SEQUENCE: 32
```

```
atggattcga aatatcagtg tgtgaag                                         27
```

<210> SEQ ID NO 33
<211> LENGTH: 26
<212> TYPE: DNA
<213> ORGANISM: Artificial
<220> FEATURE:
<223> OTHER INFORMATION: Reverse primer for AKR1C1

<400> SEQUENCE: 33

```
atattcatca gaaaatggat aattag                                          26
```

<210> SEQ ID NO 34
<211> LENGTH: 1845
<212> TYPE: DNA
<213> ORGANISM: Homo sapiens

<400> SEQUENCE: 34

```
atggacggga aggtggcagt gcaagagcgt gggcctcctg cggtctcctg ggtccccgag      60
gagggagaga agttggacca ggaagacgag gaccaggtga aggatcgggg ccaatggacc     120
aacaagatgg agtttgtgct gtcagtggcc ggggagatca ttgggctggg caatgtctgg     180
aggtttccct atctctgcta caaaaacgga ggtggagcct tcttcatccc ctacttcatc     240
ttcttctttg tctgcggcat cccggtgttc ttcctggagg tggcgttggg ccaatacacc     300
agccaaggga gtgtcacagc ctggaggaag atctgccccc tcttccaggg cattggtctg     360
gcatctgtgg tcatcgagtc atatttgaat gtctactaca tcatcatcct tgcctgggct     420
ctcttctacc tgttcagctc cttcacttct gagctgccct ggacgacctg caacaacttt     480
tggaacacag agcattgcac ggactttctg aaccactcag gagccggcac agtgaccccca    540
tttgagaatt ttacctcacc tgtcatggaa ttctgggaga cgagttct gggcatcacc      600
tcgggcatcc atgacctggg ctccctgcgc tgggagctgg ccctgtgcct cctgctcgcc     660
tgggtcatct gctatttctg catctggaag ggggtcaagt ccacaggcaa ggtggtttat     720
ttcacagcca cgtttccgta cctgatgctt gtcattttgc tgatcagagg tgtcacccttt    780
cccggagcct accagggcat catctactac ttgaagccag atttgttccg cctcaaggac     840
cctcaggtgt ggatggatgc gggcacccag atcttcttct cctttgccat ctgccagggg    900
tgcctgacag ccctgggcag ctacaacaag tatcacaaca actgctacaa ggactgcatc     960
gccctctgct tcctgaacag tgccaccagc tttgtggctg gtttgttgt cttctccatc    1020
ctgggcttca tgtcccaaga gcaagggggtg cccattttctg aagtggccga gtcaggtcct   1080
gggctggcct tcatcgcctt ccccaaggct gtgactatga tgcccttatc ccagctgtgg    1140
tcctgcctgt tctttatcat gctcatattc ctagggctgg acagccagtt tgtctgtgtg    1200
gagtgcctgg tgacagcctc catagacatg ttccccaggc agctccggaa gagcgggcgg   1260
cgcgagctcc tcatcctcac catcgccgtc atgtgctacc tgataggct tttcctggtc    1320
accgagggcg ggatgtacat cttccagctg tttgactact atgcttccag tggcatatgc    1380
ctgctgttcc tgtcattgtt tgaagtggtc tgcataagct gggtgtatgg ggcggaccgt   1440
ttctatgaca acattgagga catgattggc taccggccat ggcccctggt gaagatctcc    1500
tggctcttcc tgacccctgg actttgcctg ccactttcc tcttctcctt gagcaagtac     1560
accccccctca agtacaacaa cgtctatgtg tacccgccct ggggatactc cattggctgg    1620
ttcctggctc tgtcctccat ggtctgtgtc ccactcttcg tcgtcatcac cctcctgaag    1680
actcgggggtc ctttcaggaa gcgtctgcgt cacgtcatca ccctgactc cagtctgcca    1740
```

-continued

```
cagcccaagc aacatccctg cttggatggc agtgctggcc ggaactttgg gccctcccca      1800
acaagggaag gactgatagc cggggagaag gagacccatt tgtag                    1845

<210> SEQ ID NO 35
<211> LENGTH: 972
<212> TYPE: DNA
<213> ORGANISM: Homo sapiens

<400> SEQUENCE: 35
atggattcga aatatcagtg tgtgaagctg aatgatggtc acttcatgcc tgtcctggga       60
tttggcacct atgcgcctgc agaggttcct aaaagtaaag ctttagaggc caccaaattg      120
gcaattgaag ctggcttccg ccatattgat tctgctcatt tatacaataa tgaggagcag      180
gttggactgg ccatccgaag caagattgca gatggcagtg tgaagagaga agacatattc      240
tacacttcaa agctttggtg caattcccat cgaccagagt tggtccgacc agccttggaa      300
aggtcactga aaaatcttca attggattat gttgacctct accttattca ttttccagtg      360
tctgtaaagc caggtgagga agtgatccca aaagatgaaa atggaaaaat actatttgac      420
acagtggatc tctgtgccac atgggaggcc gtggagaagt gtaaagatgc aggattggcc      480
aagtccatcg gggtgtccaa cttcaaccgc aggcagctgg agatgatcct caacaagcca      540
gggctcaagt acaagcctgt ctgcaaccag gtggaatgtc atccttactt caaccagaga      600
aaactgctgg atttctgcaa gtcaaaagac attgttctgg ttgcctatag tgctctggga      660
tcccaccgag aagaaccatg ggtggacccg aactccccgg tgctcttgga ggacccagtc      720
ctttgtgcct tggcaaaaaa gcacaagcga accccagccc tgattgccct gcgctaccag      780
ctacagcgtg gggttgtggt cctggccaag agctacaatg agcagcgcat cagacagaac      840
gtgcaggtgt ttgaattcca gttgacttca gaggagatga aagccataga tggcctaaac      900
agaaatgtgc gatatttgac ccttgatatt tttgctggcc ccctaattaa tccattttct      960
gatgaatatt aa                                                         972
```

HEPATITIS C VIRUS INHIBITORS

BACKGROUND OF THE INVENTION

1. Field of the Invention

The present invention relates to viral inhibitors that prevent the replication of hepatitis C virus by inhibiting host factors involved in the replication of hepatitis C virus, BGT-1 and/or AKR1.

2. Background Art

Hepatitis C virus (HCV) is the major causal agent of post-transfusion non-A, non-B hepatitis and the hepatitis caused by this virus is often chronic. The cDNA of this virus was cloned in 1989 by Choo et al. (Choo, Q. L. et al., Science, 244, 359-362, 1989), and the virus is known as a single-stranded RNA virus belonging to the Flavivirus family (Kato, N. et al., Proc. Natl. Acad. Sci. USA, 87, 9524-9528, 1990). The complete nucleotide sequence and corresponding amino acid sequence were explained by several groups. We previously prepared a vector that expresses the full-length HCV gene (WO99/67394).

There is an urgent need to discover a therapeutic means for hepatitis C, partially because any medicine showing a complete anti-viral effect has not been established. Currently, the most effective treatment is a combination therapy with pegylated interferon and Ribavirin. However, a complete response to even this therapy is achieved in only about 50% of patients infected with HCV genotype 1b for which many antibody-positive patients exist in Japan and interferon is less effective, and it would be highly desirable to develop a new antiviral agent. It is said that 170,000,000 HCV-positive patients exist in the world including 2,000,000 or more patients in Japan and the progression of hepatitis C to liver cancer or cirrhosis occurs at high probability so that a therapeutic means must be urgently established. Attempts were previously made to develop antiviral drugs based on the inhibition of the protease activity of nonstructural proteins involved in the replication of HCV (NS3, NS5) or the like, but any sufficient effect has not been achieved due to a large number of mutations in the virus gene and other reasons.

Among four subtypes of the inhibitory neurotransmitter GABA transporter, only BGT-1 (betaine/GABA transporter 1) has affinity for betaine. Betaine is one of substances called compatible solutes, which are synthesized to restore osmotic balance between the inside and outside of a cell and narrowly refers to trimethylglycine. In 1992, it was cloned from MDCK cells derived from dog kidney (Yamauchi et al., J. Biol. Chem. 267, 649-652, 1992). BGT-1 is peripherally expressed mainly in kidney and liver, and occurs in astroglia in the cerebellum, cerebral cortex, brain stem and the like in the central nervous system. However, BGT-1 is not always expressed near GABAergic neurons, suggesting that BGT-1 is more likely to be involved in the removal of GABA escaping from the synapse or osmoregulation rather than the termination of neurotransmission of GABAergic neurons. Any relation to HCV has not been reported.

AKR1C1 (Aldo-Keto Reductase Family 1) functions to convert an aldehyde or a ketone into an alcohol by utilizing NADH or NADPH and exists as a monomer (around 35 kDa) in the cytoplasm. It is highly expressed in liver along with AKR1C4 (Steckelbroeck, S. et al., J. Pharm. Exp. Ther. 316, 1300-1309, 2006). It is reported to be absent in breast cancer or the like (Ji, Q et al., Cancer Research 64, 7610-7617, 2004). It is also reported that the expression of AKR1C1 was decreased by a nonstructural protein of HCV, NS4B (Zheng, Y et al., J. Biochem. Mol. Biol. 38, 151-160, 2005).

Recently, a method for inhibiting the expression of a specific gene in a cell in an animal body was found, which comprises inhibiting the expression of the target gene using a double-stranded RNA against the target gene (Fire A et al., Nature 391:806-811 (1998)). This method is called RNA interference (RNAi), and based on the phenomenon that when a double-stranded RNA (dsRNA) is introduced into a cell, an mRNA corresponding to the RNA sequence in the cell is specifically degraded and no more expressed as a protein. RNAi is an effective method for studying the functions of novel genes by inhibiting their expression and extensively used for gene function analysis of nematodes, drosophilas, etc. However, it has been unknown whether or not RNAi is effective for the treatment of diseases, especially viral diseases such as hepatitis C.

DISCLOSURE OF THE INVENTION

Problems to be Solved by the Invention

The present invention aims to provide HCV inhibitors capable of inhibiting viral replication in HCV-infected cells.

Means for Solving the Problems

We previously prepared an anti-DHCR24 antibody (WO2005/019268), and found that it has an inhibitory effect against HCV replication (WO2007/097461). Thus, we analyzed molecules showing decreased expression after adding the anti-DHCR24 antibody to HCV-replicating cells on microarrays to identify them as GABA transporter (BGT-1) and AKR1C1. Then, we found that when the expression of these molecules was decreased by their siRNAs, the replication of HCV significantly declined. The present invention was accomplished on the basis of these findings.

Accordingly, the present invention provides a hepatitis C virus inhibitor comprising a substance inhibiting BGT-1.

The present invention also provides a hepatitis C virus inhibitor comprising a substance inhibiting AKR1C1.

The present invention also provides an siRNA of the BGT-1 gene consisting of the nucleotide (a), (b), or (c) below:

(a) an nucleotide consisting of the nucleotide sequence 5'-CAACAAGAUGGAGUUUGUGCUGUCA-3' (SEQ ID NO: 1);

(b) an nucleotide of 25-40 nucleotides in length including the nucleotide sequence 5'-CAACAAGAUGGAGUUU-GUGCUGUCA-3' (SEQ ID NO: 1); or (c) an nucleotide capable of hybridizing an nucleotide consisting of a nucleotide sequence complementary to an nucleotide consisting of the nucleotide sequence of SEQ ID NO: 1 under stringent conditions and capable of inhibiting the replication of hepatitis C virus.

The present invention also provides an siRNA of the AKR1C1 gene consisting of the nucleotide (a), (b), or (c) below:

(a) an nucleotide consisting of the nucleotide sequence 5'-AAGUAAAGCUUUAGAGGCCACCAAA-3' (SEQ ID NO: 13);

(b) an nucleotide of 25-40 nucleotides in length including the nucleotide sequence 5'-AAGUAAAGCUUUAGAGGC-CACCAAA-3' (SEQ ID NO: 13); or (c) an nucleotide capable of hybridizing an nucleotide consisting of a nucleotide sequence complementary to an nucleotide consisting of the nucleotide sequence of SEQ ID NO: 13 under stringent conditions and capable of inhibiting the replication of hepatitis C virus.

The present invention also provides an siRNA of the AKR1C1 gene consisting of an nucleotide of 19-40 nucleotides in length specifically acting on an mRNA corresponding to an nucleotide consisting of the nucleotide sequence shown by SEQ ID NO: 22 and capable of inhibiting the replication of hepatitis C virus.

BRIEF DESCRIPTION OF THE DRAWINGS

FIG. 5 represents graphs showing the results of an analysis of cytotoxic activity against HCV-replicating cells after incubation of (A) FLR3-1 cells and (B) R6FLR-N cells with a rabbit anti-BGT-1 polyclonal antibody or a mouse anti-AKR1C1 polyclonal antibody for 72 hours (n=3). "−" represents a group incubated without antibody, and normal mouse serum was used as a control of the anti-AKR1C1 antibody and normal rabbit serum was used as a control of the anti-BGT-1 antibody.

PREFERRED EMBODIMENTS OF THE INVENTION

Figure 1:
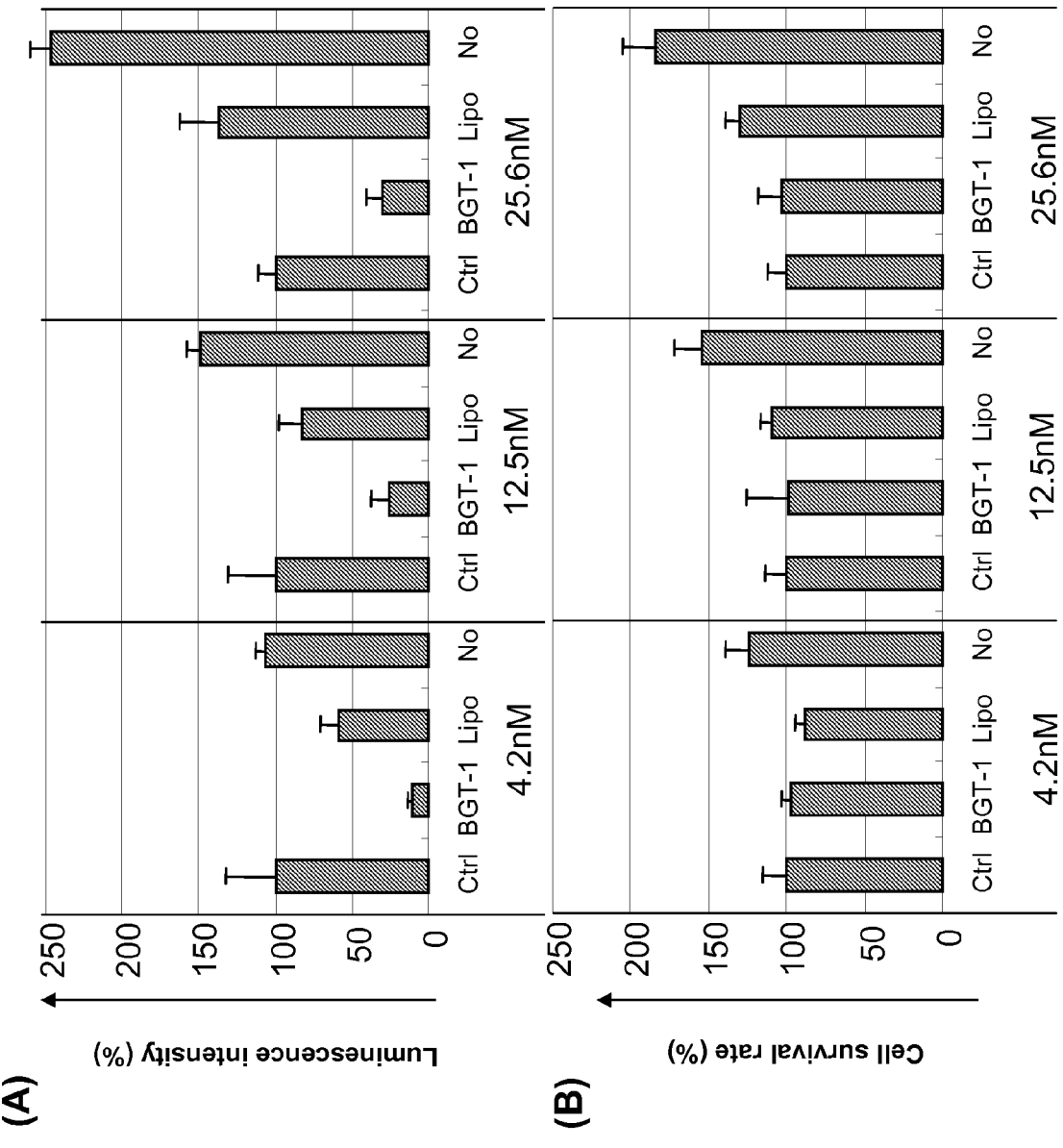
FIG. 1 represents graphs showing the results of an analysis of (A) inhibitory activity against HCV replication and (B) cytotoxic activity against HCV-replicating cells after incubation of R6FLR-N cells with an siRNA of BGT-1 ("BGT-1") for 72 hours (n=3). In the figure, "Ctrl" represents a group treated with a control siRNA, "Lipo" represents a group incubated with Lipofectamine alone without siRNA, and "No" represents a group incubated in culture medium alone. The values in the control siRNA group are defined as 100%.

The present invention provides hepatitis C virus inhibitors comprising a substance inhibiting BGT-1 and/or a substance inhibiting AKR1C1. The substance inhibiting BGT-1 or AKR1C1 may be any substance having the ability to inhibit the expression or to lower the activity of BGT-1 or AKR1C1, and is not limited to any source or shape. The inhibitory substance may be an siRNA, antibody, inhibitor or the like. Preferably, its interaction to BGT-1 or AKR1C1 is specific.

Thus, the term "inhibitory substance" as used herein refers to a substance that inhibits the expression or inhibits the activity of the BGT-1 or AKR1C1 gene or corresponding protein. The term "viral inhibitor" refers to a drug that inhibits viral replication or injures virus-infected cells.

The inhibitory effect against HCV replication can be determined by using HCV replicon cells (Lohmann et al., Science, 1999, 285 (5424):110-113). HCV replicon cells bear a luciferase gene as an indicator gene fused to a nonstructural protein (NS) region necessary for the replication of HCV. HCV replication activity can be measured by luciferase assays. Viral inhibitory activity can also be evaluated by using HCV infection systems (Wakita et al., Nat. Med. 2005, 11 (7), 791-796).

Inhibitory substances are explained below.

1. siRNAs

The siRNAs of the present invention may be synthesized or expressed by using expression vectors so far as they can inhibit the replication of hepatitis C virus by inhibiting the expression of BGT-1 or AKR1C1.

The siRNAs of the present invention may be single- or double-stranded, or may be formed of two or more strands, but they are preferably double-stranded. The double strand may be formed of two independent strands or formed within a self-complementary single-stranded RNA. In the case of double-stranded siRNAs, they may form a double strand in all regions or may partially contain single strands or the like (e.g., at both ends or one end).

The length of the siRNAs of the present invention is not limited so far as they have the ability to bind the mRNA of BGT-1 or AKR1C1. The length of the siRNAs of the present invention is e.g., 5-1000 nucleotides (5-1000 bp in the case of double strands), preferably 10-100 nucleotides (10-100 bp in the case of double strands), more preferably 15-25 nucleotides (15-25 bp in the case of double strands).

For example, siRNAs of BGT-1 include the nucleotides of SEQ ID NOS: 1-10. The nucleotide of SEQ ID NO: 1 is preferred. Nucleotides of 25-40 nucleotides in length including the nucleotide sequence of SEQ ID NO: 1 can also be used. Nucleotides containing one to several (e.g., two, three, four or five) deletions, substitutions, and/or additions in the nucleotide sequence of SEQ ID NO: 1 can also be used. Specifically, any nucleotide capable of hybridizing an nucleotide consisting of a nucleotide sequence complementary to an nucleotide consisting of the nucleotide sequence of SEQ ID NO: 1 under stringent conditions and capable of inhibiting the replication of hepatitis C virus can be used as the siRNAs of the present invention. Exemplary siRNAs of the BGT-1 gene are described in Table 1 below.

TABLE 1 siRNAs of the BGT-1 gene

| SEQ ID NO: | Sequence | Nucleotide No.* |
|---|---|---|
| 1 | CAACAAGAUGGAGUUUGUGCUGUCA | 120-144 |
| 2 | CAUCUGUGGUCAUCGAGUCAUAUUU | 362-386 |
| 3 | CAGAGCAUUGCACGGACUUUCUGAA | 488-512 |
| 4 | GGUGGUUUAUUUCACAGCCACGUUU | 711-735 |
| 5 | CCACGUUUCCGUACCUGAUGCUUGU | 728-752 |
| 6 | CAUCUACUACUUGAAGCCAGAUUUG | 801-825 |
| 7 | AGCUGUGGUCCGCCUGUUCUUUAU | 1133-1157 |
| 8 | UGCCUGUUCUUUAUCAUGCUCAUAU | 1144-1168 |
| 9 | GCCUGUUCUUUAUCAUGCUCAUAUU | 1145-1169 |
| 10 | UCAAGUACAACAACGUCUAUGUGUA | 1568-1592 |

*Based on the BGT-1 coding region (SEQ ID NO: 34).

For example, siRNAs of AKR1C1 include the nucleotides of SEQ ID NOS: 11-21. The nucleotide consisting of SEQ ID NO: 13 is preferred. Nucleotides of 25-40 nucleotides in length including the nucleotide sequence of SEQ ID NO: 13 can also be used. Nucleotides containing one to several (e.g., two, three, four or five) deletions, substitutions, and/or additions in the nucleotide sequence of SEQ ID NO: 13 can also be used. Specifically, any nucleotide capable of hybridizing an nucleotide consisting of a nucleotide sequence complementary to an nucleotide consisting of the nucleotide sequence of SEQ ID NO: 13 under stringent conditions and capable of inhibiting the replication of hepatitis C virus can be used as the siRNAs of the present invention. Alternatively, nucleotides of 19-40 nucleotides in length specifically acting on an mRNA corresponding to an nucleotide consisting of the nucleotide sequence shown by SEQ ID NO: 22 (AAAAG-TAAAG CTTTAGAGGC CACCAAATTG GCAATTGAAG CTGGCTTCCG CCATATTGAT TCTGCTCATT TATA-CAATAA) can also be used as siRNAs of AKR1C1. Specifically, the nucleotides of SEQ ID NOS: 13-17 can be used. Exemplary siRNAs of the gene are described in Table 2 below.

TABLE 2 siRNAs of the AKR1C1 gene

| SEQ ID NO: | Sequence | Nucleotide No.* |
|---|---|---|
| 11 | UGGAUUCGAAAUAUCAGUGUGUGAAGCUGAAU | 2-33 |
| 12 | CGAAAUAUCAGUGUGUGAAGCUGAA | 8-32 |
| 13 | AAGUAAAGCUUUAGAGGCCACCAAA | 93-117 |
| 14 | AGUAAAGCUUUAGAGGCCACCAAAU | 94-118 |
| 15 | AGAGGCCACCAAAUUGGCAAUUGAA | 105-129 |
| 16 | GCAAUUGAAGCUGGCUUCCGCCAUA | 121-145 |

TABLE 2-continued siRNAs of the AKR1C1 gene

| SEQ ID NO: | Sequence | Nucleotide No.* |
|---|---|---|
| 17 | CCGCCAUAUUGAUUCUGCUCAUUUA | 138-162 |
| 18 | UGGAUUAUGUUGACCUCUACCUUAU | 323-347 |
| 19 | UGUCUGCAACCAGGUGGAAUGUCAU | 558-582 |
| 20 | GCAUCAGACAGAACGUGCAGGUGUU | 827-851 |
| 21 | GCCUAAACAGAAAUGUGCGAUAUUU | 893-917 |

*Based on the AKR1C1 coding region (SEQ ID NO: 35).

The "stringent conditions" here can be determined as appropriate by those skilled in the art by reference to the description of Maniatis, T., Fritsch, E. F. & Sambrook, J., Molecular Cloning: A Laboratory Manual, Second Edition (Cold Spring Harbor Laboratory Press, New York, 1989), and include the following conditions by way of example: incubation in 6×SSC (pH 7.0) containing 0.5% SDS, 5×Denhardt's solution and 100 μg/ml salmon sperm DNA, at 42° C. or more, e.g., 50° C.-65° C. or 65-70° C. for 4 hours to overnight, followed by washing in 0.1×SSC-6×SSC, preferably 0.1× SSC-2×SSC, more preferably 0.2×SSC at room temperature for 10 minutes, in 2×SSC containing 0.1% SDS at room temperature for 10 minutes, and in 0.2×SSC containing 0.1% SDS at 68° C. for 20 minutes.

The siRNAs used in the present invention are not specifically limited, and not only unmodified normal RNAs but also RNAs modified at the phosphate diester or carbohydrate moiety can also be used. Moreover, the siRNAs of the present invention may partially contain non-RNA molecules such as DNA.

The siRNAs of the present invention can be prepared by methods known to those skilled in the art. Specifically, the siRNAs used in the present invention can be synthesized by known methods. They can also be incorporated into Lentivirus vectors by known methods in such a manner that they can be expressed in cells. In addition, various known delivery systems for delivering siRNAs into organisms to allow them to act (viral vectors, liposomes, atelocollagen, etc.) can also be used.

The siRNAs of the present invention can be formulated into tablets, powders, granules, capsules, liposome capsules, injection formulations, liquid formulations, nasal drops, etc., optionally in conjunction with excipients, isotonizing agents, solubilizers, stabilizers, preservatives, soothing agents, etc. They can be formed into lyophilized formulations. These can be routinely prepared.

The siRNAs of the present invention are mixed with e.g., liposome or atelocollagen and applied to the affected area of a patient directly or by intravascular administration or other means allowing them to reach the affected area. For example, they can be administered orally, intraperitoneally or via intravenous injection. They can also be administered by using encapsulating materials for prolonged action or increased membrane permeability such as liposomes, poly-L-lysine, lipids, cholesterol, lipofectin or derivatives thereof.

The siRNAs of the present invention can be administered at a preferable dose adapted as appropriate for the condition of a patient. For example, they can be administered in a range of 0.001-100 mg/kg, preferably 0.1-10 mg/kg. The siRNAs are preferably administered once or more a week because they are effective for at most one week in view of their stability.

2. Antibodies

When the substance inhibiting BGT-1 and/or the substance inhibiting AKR1C1 is an antibody, the antibody used in the present invention may be polyclonal or monoclonal so far as it can inhibit the replication of hepatitis C virus by inhibiting the activity of BGT-1 or AKR1C1. Preferably, it is a monoclonal antibody.

The antibody of the present invention may be derived any animal such as mouse, human, rat, rabbit, sheep, camel or the like.

Moreover, it may be any antibody including variant antibodies having a substituted amino acid sequence such as chimeric antibodies or humanized antibodies, modified antibodies having various molecules attached thereto, antibody fragments, truncated antibodies, antibodies with modified glycosylation patterns, etc. For example, examples of antibody fragments include Fab, F(ab')$_2$, Fv, Fab/c having one Fab and a complete Fc, or single-chain Fv (scFv) consisting of heavy and light chain Fvs joined by a linker, diabodies, etc.

Anti-BGT-1 antibodies and anti-AKR1C1 antibodies used in the present invention can be obtained as polyclonal or monoclonal antibodies by known means. The anti-BGT-1 antibodies and anti-AKR1C1 antibodies used in the present invention are preferably monoclonal antibodies, especially derived from mammals. Monoclonal antibodies derived from mammals include those produced by hybridomas, and those produced by hosts transformed with an expression vector containing the antibody gene by genetic engineering techniques. Such antibodies can be obtained by methods known to those skilled in the art.

Modified antibodies include anti-BGT-1 antibodies or anti-AKR1C1 antibodies conjugated to various molecules such as cytotoxic agents or polyethylene glycol (PEG). Cytotoxic agents include, e.g., radioisotopes, chemotherapeutic agents, cellular toxins, etc. Modified antibodies conjugated to such other substances are also included in the "antibodies" in the present invention.

The antibodies used in the present invention may also be bispecific antibodies. The bispecific antibodies may have antigen-binding sites recognizing different epitopes on the BGT-1 or AKR1C1 molecule or may have one antigen-binding site recognizing BGT-1 or AKR1C1 and another antigen-binding site recognizing a cytotoxic agent such as a chemotherapeutic agent, cellular toxin, radioisotope or the like.

When such an antibody is used as a viral inhibitor, the effective unit dose is selected in the range of 0.001 mg to 1,000 mg/kg body weight, or alternatively, in the range of 0.01 to 100,000 mg/body per patient. However, the dose levels of viral inhibitors containing an anti-BGT-1 antibody and/or an anti-AKR1C1 antibody are not limited to these ranges.

The viral inhibitors can be administered e.g., 1-3 times per day for 1-7 days per week before or after a clinical symptom of the disease appears.

The viral inhibitors of the present invention are typically administered via parenteral routes including, but not limited to, injection (e.g. subcutaneous, intravenous, intramuscular or intraperitoneal injection), but may also be administered via percutaneous, mucosal, nasal, pulmonary or oral route.

The viral inhibitors of the present invention containing an anti-BGT-1 antibody and/or an anti-AKR1C1 antibody as an active ingredient can be routinely formulated (see e.g., Remington's Pharmaceutical Science, latest edition, Mark Publishing Company, Easton, USA) optionally in conjunction with pharmaceutically acceptable carriers and additives.

Examples of such carriers and pharmaceutical additives include water, pharmaceutically acceptable organic solvents, collagen, polyvinyl alcohol, polyvinyl pyrrolidone, carboxy vinyl polymers, sodium carboxymethyl cellulose, sodium polyacrylate, sodium alginate, water-soluble dextran, sodium carboxymethyl starch, pectin, methyl cellulose, ethyl cellulose, xanthan gum, arabic gum, casein, agar, polyethylene glycol, diglycerin, glycerin, propylene glycol, vaseline, paraffin, stearyl alcohol, stearic acid, human serum albumin (HSA), mannitol, sorbitol, lactose, pharmaceutically acceptable surfactants, etc.

In practice, the carriers and additives listed above are selected alone or in combination as appropriate depending on the dosage form of a particular viral inhibitor of the present invention, but are not limitative. For example, solutions containing a purified anti-BGT-1 antibody and/or anti-AKR1C1 antibody dissolved in a solvent such as physiological saline, buffer, glucose solution or the like in conjunction with an adsorption inhibitor such as Tween 80, Tween 20, gelatin, human serum albumin or the like can be used as injection formulations. Alternatively, lyophilized formulations to be dissolved/reconstituted before use can be prepared with lyophilization excipients including sugar alcohols and sugars such as mannitol, glucose, etc.

3. Inhibitors

When the substance inhibiting BGT-1 and/or the substance inhibiting AKR1C1 is an inhibitor, the inhibitor used in the present invention may be any compound so far as it can inhibit the replication of hepatitis C virus by inhibiting the activity of BGT-1 or AKR1C1.

Inhibitors of BGT-1 that can be used include, e.g., glycine transporter inhibitors such as 1-(3-(9H-carbazol-9-yl)-1-propyl)-4-(2-methoxyphenyl)-4-piperidinol (NNV05-2090) (Soudijn, W. and Wingaarden, I. van, Current Medical Chemistry, 7, 1063-1079, 2000), NNC05-2090, and tiagabine.

Inhibitors of AKR1C1 that can be used include, e.g., flufenamic acid (Steckelbroeck, S. et al., J. Pharm. Exp. Therap, 316, 1300-1309, 2006).

Viral inhibitors of the present invention comprising a BGT-1 inhibitor and/or an AKR1C1 inhibitor are orally administered in the form of tablets at a daily dose of 32-56 mg per adult divided into 2-4 portions until their effect is produced.

The present invention also provides siRNAs of the BGT-1 gene and siRNAs of the AKR1C1 gene. The sequences, lengths and structures of the siRNAs were described above.

The present invention also relates to a method for preventing or treating a disease caused by hepatitis C virus infection, comprising administering a substance inhibiting BGT-1 and/or a substance inhibiting AKR1C1 to a patient infected with hepatitis C virus. Preferably, the substance inhibiting BGT-1 and the substance inhibiting AKR1C1 are used in combination. The inhibitory substances that can be used include the siRNAs, antibodies, inhibitors and the like as described above.

EXAMPLES

1. Identification of Genes Involved in HCV Replication

In this study, HCV-replicating cells (FLR3-1 and R6FLR-N) established from Huh-7 replicon cells (Lohmann et al., Science, 1999, 285 (5424):110-3) containing a luciferase-neo fusion gene and three HCV nonstructural protein regions (NS3-NS5b) after G418 selection were used. The use of these cells allows HCV replication activity to be measured by a luciferase assay. The HCV-replicating cells (FLR3-1 or R6FLR-N) were reverted by treatment with interferon α (100

IU/ml) for 72 hours or more to lower the HCV replication level and used as control cells (see Guo J T, Bichko V V, Seeger C., J. Virol. 2001, 75 (18):8516-23). The cells were incubated in Dulbecco's modified Eagle's medium (DMEM) GlutaMax I containing penicillin (100 U/ml), streptomycin (100 µg/ml), G418 (500 µg/ml), and 10% FCS (SIGMA).

The HCV-replicating cells (FLR3-1 and R6FLR-N) (Nakagawa, S. et al., B.B.R.C. 353, 882-888, 2006) and the reverted cells were treated with an anti-DHCR24 antibody (WO2007/097461) or normal mouse IgG1 antibody (control, Millipore) and mRNAs were extracted from these cells. Then, cDNAs were synthesized from the extracted mRNAs by reverse transcription, and the signal ratio between the groups treated with the anti-DHCR24 antibody/control antibody was determined by using Whole Human Genome Oligo DNA Microarray (Agilent Technologies, Inc.). Sequences showing low signal ratios in the reverted cells and high signal ratios in both FLR3-1 and R6FLR-N cells were analyzed to identify them as *Homo sapiens* solute carrier family 6 (betaine/GABA transporter: BGT-1), member 12 (SLC6A12, GenBank Accession Number: NM_003044), and *Homo sapiens* aldo-keto reductase family 1, member C1 (AKR1C1, GenBank Accession Number: NM_0001353).

Thus, it was shown that the expression of BGT-1 and AKR1C1 declines in the HCV-replicating cells treated with the anti-DHCR24 antibody.

2. Inhibitory Activity of siRNAs Against HCV Replication

An siRNA specifically silencing BGT-1 or AKR1C1 was prepared and reversely transfected into R6FLR-N cells. The sequences of the siRNAs used are as follows.

```
BGT-1 gene:
                                         (SEQ ID NO: 1)
siRNA:         5'-CAACAAGAUGGAGUUUGUGCUGUCA-3'

(SEQ ID NO: 23)
control siRNA: 5'-CAAAGAGGUUGAGUUCGUGUCAUCA-3'

AKR1C1 gene:
                                         (SEQ ID NO: 13)
siRNA:         5'-AAGUAAAGCUUUAGAGGCCACCAAA-3'

(SEQ ID NO: 24)
control siRNA: 5'-AAGAACGUUAUAGGGCCCACAUAAA-3'
```

The reverse transfection of the siRNAs was performed as follows. In each well of a 96-well plate (Falcon) containing Opti-MEM I medium was added each siRNA at a final concentration of 4.2, 12.6, and 25.2 nM and the plate was gently shaken. Lipofectamine™ RNAiMAX was mixed before use and added to the well (0.1 µl/well), and the plate was gently shaken and allowed to stand for 10-20 minutes at room temperature. R6FLR-N cells were plated at a density of 5×10³ cells/well and incubated at 37° C. in 5% $CO_2$ for 5 hours. The culture medium was replaced with 10% DMEM-Glutamax, and the cells were further incubated at 37° C. in 5% $CO_2$. A plate containing the medium and Lipofectamine alone without siRNA ("Lipo") and a plate containing the medium alone ("No") were used as controls.

After incubation for 24, 48, and 72 hours, the HCV replication activity was measured by a luciferase assay. The replication activity is expressed relative to the luminescence intensity in the groups treated with the control siRNAs ("Ctrl") defined as 100%. The experiment was performed in triplicate, and the average±S.D. was graphically shown. Statistical analysis was performed by Student's t-test.

In R6FLR-N cells treated with the siRNA of BGT-1 ("BGT-1"), the replication of HCV declined to 10±4% or less even at 4.2 nM siRNA at 72 hours post-treatment (FIG. 1A, Ctrl vs. BGT-1, $p<0.05$).

Figure 2:
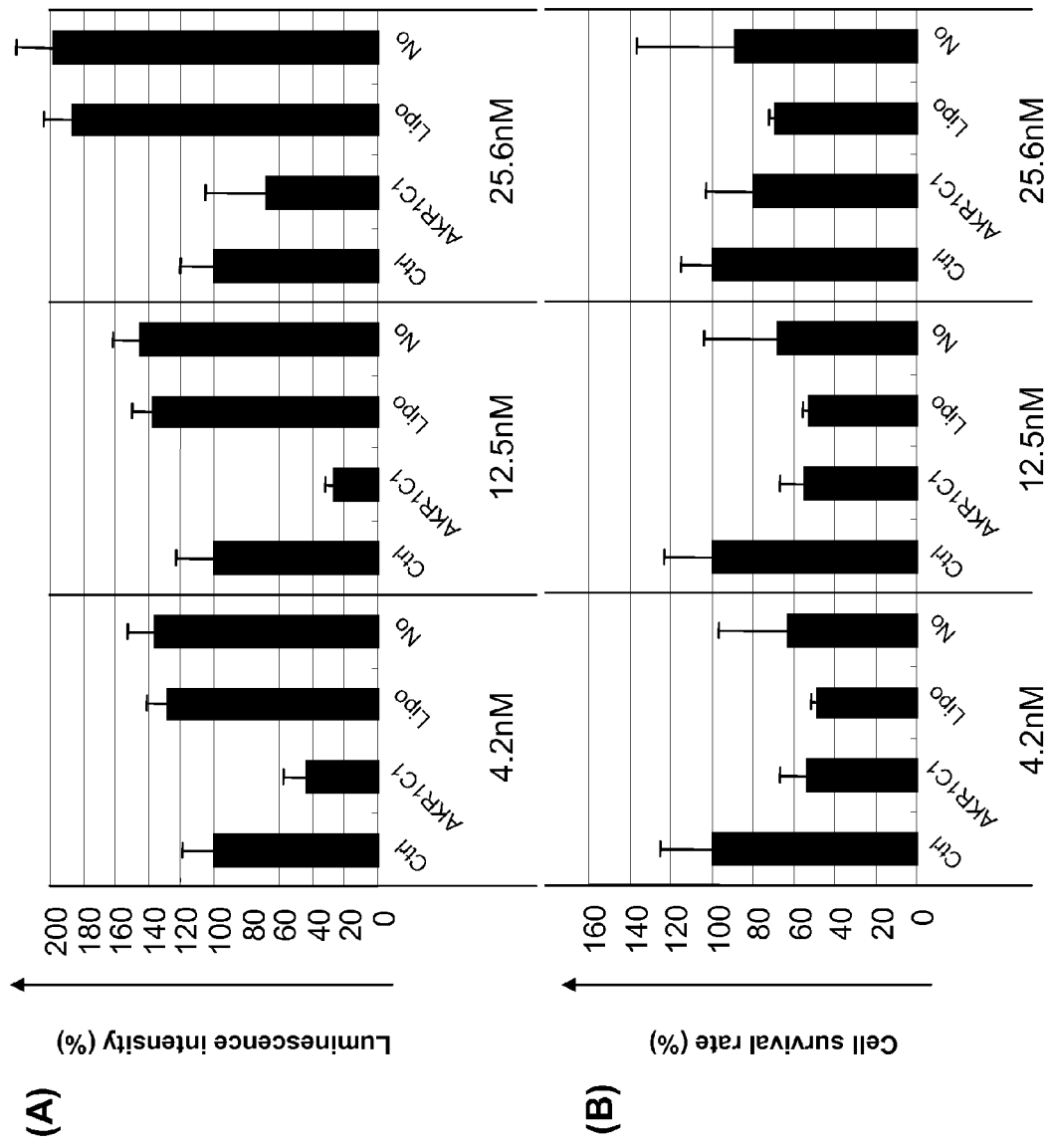
FIG. 2 represents graphs showing the results of an analysis of (A) inhibitory activity against HCV replication and (B) cytotoxic activity against HCV-replicating cells after incubation of R6FLR-N cells with an siRNA of AKR1C1 ("AKR1C1") for 72 hours (n=3). In the figure, "Ctrl" represents a group treated with a control siRNA, "Lipo" represents a group incubated with Lipofectamine alone without siRNA, and "No" represents a group incubated in culture medium alone. The values in the control siRNA group are defined as 100%.

In R6FLR-N cells treated with the siRNA of AKR1C1 ("AKR1C1"), the replication of HCV also declined to 40±1% even at 4.2 nM siRNA at 72 hours post-treatment, thus showing a significant inhibitory effect (FIG. 2A, Ctrl vs. AKR1C1, $p<0.05$).

In order to verify that the inhibitory effect of the siRNAs of BGT-1 and AKR1C1 against HCV replication does not result from any artificial inhibition by the siRNAs, two siRNAs inhibiting the expression of DHCR24 were then prepared, and the inhibitory activity against HCV replication was determined in the same manner after incubation of R6FLR-N cells (FIG. 3A) or FLR3-1 cells (FIG. 3B) with these siRNAs for 72 hours. The siRNAs prepared were an siRNA against nucleotides 417-435 ("DHCR24_417") and 1024-1042 ("DHCR24_1024") of the DHCR24 gene. An siRNA against a variant p53 gene (p53m2) was used as a negative control, and siRNAs against HCV were used as positive controls. An siRNA of HCV (R5) was used for HCV type 1b, and an siRNA of HCV (R7) was used for HCV type 2a. The sequences of the siRNAs used are shown below.

```
siRNA of p53m2:
5'-GACUCCAGUGAUAAUCUGCUU-3'     (SEQ ID NO: 25)

siRNA of HCV (R5):
5'-GUCUCGUAGACCGUGCAUCAUU-3'    (SEQ ID NO: 26)

siRNA of HCV (R7):
5'-GUCUCGUAGACCGUGCACCATT-3'    (SEQ ID NO: 27)

siRNA of DHCR24 (417-435):
5'-GUACAAGAAGACACACAAAUU-3'     (SEQ ID NO: 28)

siRNA of DHCR24 (1024-1042):
5'-GAGAACUAUCUGAAGACAAUU-3'.    (SEQ ID NO: 29)
```

As a result, the siRNAs of HCV (R5 or R7) showed a significant inhibitory effect against HCV replication at 0.1 nM, but the siRNAs of DHCR24 at 1.0 nM or more were required to produce a significant inhibitory effect against HCV replication (FIGS. 3A and 3B), in contrast to the minimal effective concentration of 0.5 nM at which the siRNAs of BGT-1 and AKR1C1 show a significant inhibitory effect against HCV replication vs. the control siRNAs (data not shown). Thus, it was verified that the siRNAs of BGT-1 and AKR1C1 inhibit the replication of HCV more effectively than the siRNAs of DHCR24 and that this does not result from any artificial inhibition by the siRNAs.

3. Cytotoxic Activity of siRNAs Against HCV-Replicating Cells

In the same manner as described above, the siRNA were reversely transfected into R6FLR-N cells in a 96-well plate (Falcon). After incubation for 24, 48, and 72 hours, the number of viable cells was counted by a chromogenic reaction at 37° C. for 1 hour using Cell Counting Kit-8 (DOJINDO) following the manufacturer's protocol. The results are expressed relative to the cell survival rate in the groups treated with the control siRNAs defined as 100%. The experiment was performed in triplicate, and the average±S.D. was graphically shown. Statistical analysis was performed by Student's t-test.

As a result, any significant cytotoxic activity was not detected in the cells treated with the siRNA of BGT-1 at any siRNA concentration tested (FIG. 1B).

In the cells treated with the siRNA of AKR1C1, the cell survival rate declined to 53±18% even at 4.2 nM siRNA at 72 hours post-treatment, thus showing a significant cytotoxic activity (FIG. 2B, $p<0.05$).

Then, R6FLR-N cells or FLR3-1 cells were incubated with the siRNAs of HCV or DHCR24 described above for 72 hours, and the cytotoxic activity against HCV-replicating cells was determined in the same manner.

Figure 3:
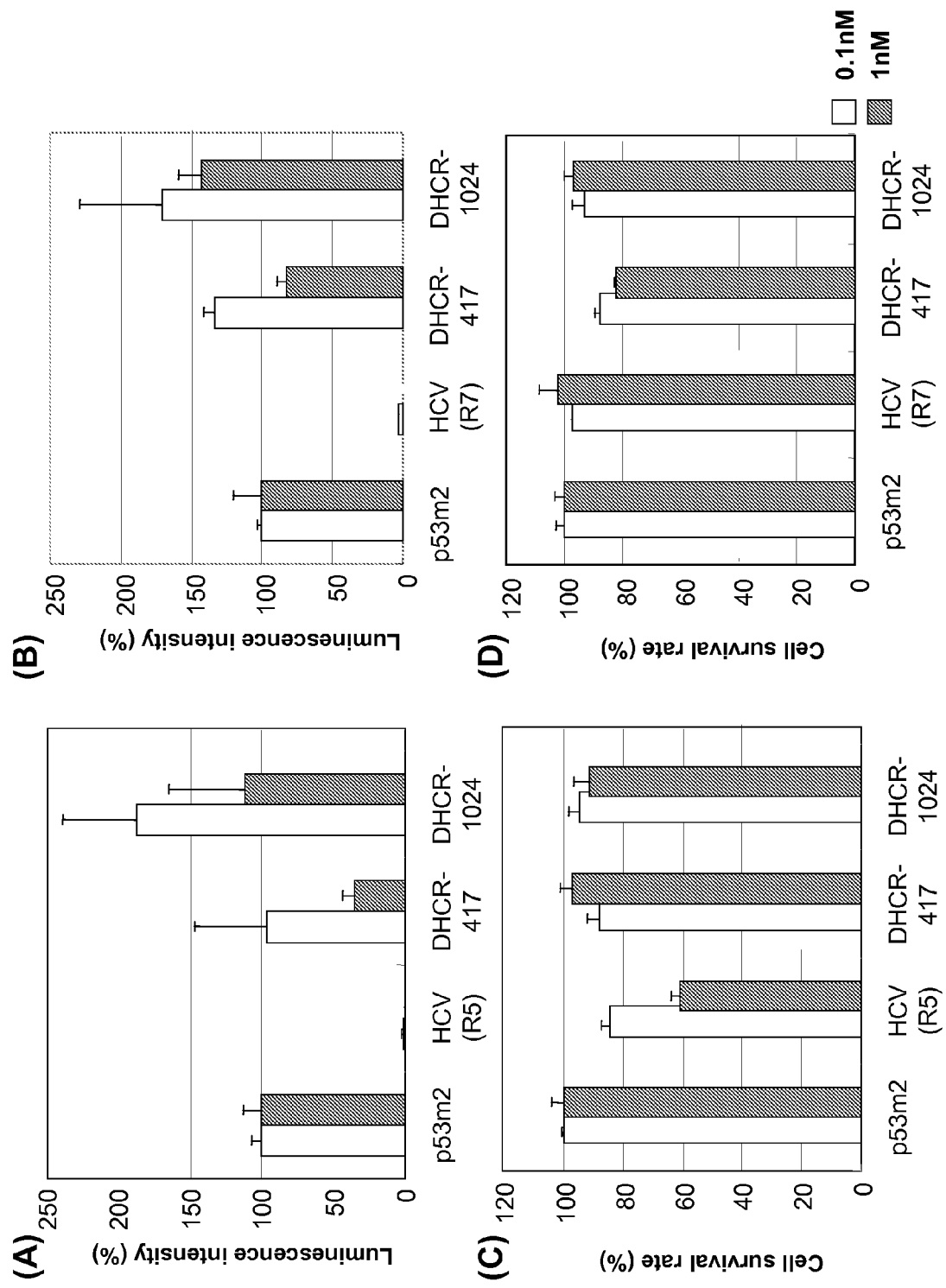
FIG. 3 represents graphs showing the results of an analysis of inhibitory activity against HCV replication (A and B) and cytotoxic activity against HCV-replicating cells (C and D) after incubation of R6FLR-N cells (A and C) or FLR3-1 cells (B and D) with HCV (R5 or R7) and siRNAs of DHCR24 for 72 hours (n=3). The values are expressed relative to the values in the group treated with an siRNA against a variant p53 gene (p53m2) defined as 100%.

As a result, the cell survival rate in the presence of the siRNA of HCV (R5) at a concentration of 1.0 nM declined to 60%, thus showing a cytotoxic activity, but the cell survival rate in the presence of the siRNAs of DHCR24 even at 1.0 nM was 82-98%, thus showing little cytotoxic activity (FIGS. 3C and D). Thus, it was shown that the siRNA of AKR1C1 injures the HCV-replicating cells with significantly higher efficiency than the siRNAs of DHCR24.

4. Verification of the Expression Inhibitory Effect of siRNAs by Western Blotting and PCR The expression of BGT-1 and AKR1C1 and the inhibition of the expression by their siRNAs were analyzed by Western blotting and PCR.

A rabbit anti-BGT-1 polyclonal antibody (abcam) and a mouse anti-AKR1C1 polyclonal antibody (Abnova) were used as 1:5000 and 1:2500 dilutions in 3% BSA/PBS, respectively. HRP-conjugated secondary antibodies (an anti-mouse antibody (Invitrogen), and an anti-rabbit antibody (DAKO)) were used as 1:5000 dilutions in 3% BSA/PBS. The expression of BGT-1 and AKR1C1 was detected by using ECL Plus Western Blotting Detection Reagents (Amersham Biosciences) following the manufacturer's protocol to verify siRNA-induced silencing (data not shown).

The inhibition of the expression of the BGT-1 gene and the AKR1C1 gene by their siRNAs was also verified by RT-PCR using the following primers (data not shown):

```
BGT-1
Forward:
5'-ATGGACGGGAAGGTGGCAGTGCAAGAG-3'    (SEQ ID NO: 30)

Reverse:
5'-CAAATGGGTCTCCTTCTCCCCGGCTAT-3'    (SEQ ID NO: 31)

AKR1C1
Forward:
5'-ATGGATTCGAAATATCAGTGTGTGAAG-3'    (SEQ ID NO: 32)

Reverse:
5'-ATATTCATCAGAAAATGGATAATTAG-3'.    (SEQ ID NO: 33)
```

5. Inhibitory Activity of Antibodies Against HCV Replication

FLR3-1 cells and R6FLR-N cells were incubated with a rabbit anti-BGT-1 polyclonal antibody (abcam) or a mouse anti-AKR1C1 polyclonal antibody (Abnova) for 72 hours. After incubation, the relative luminescence unit (RLU) was measured by a luciferase assay to evaluate the inhibitory activity against HCV replication. Normal rabbit serum was used as a control of the anti-BGT-1 antibody, and normal mouse serum was used as a control of the anti-AKR1C1 antibody. Each antibody was diluted at 1:100-1:10000 in 3% BSA/PBS. The experiment was performed in triplicate, and the average±S.D. was graphically shown. Statistical analysis was performed by Student's t-test.

Figure 4:
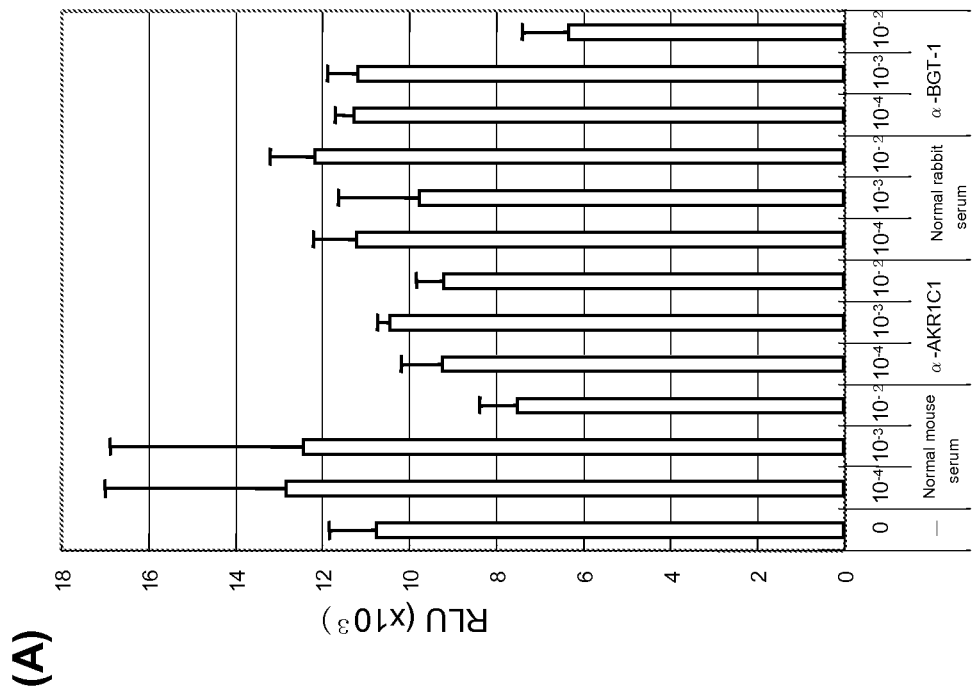
FIG. 4 represents graphs showing the results of an analysis of inhibitory activity against HCV replication after incubation of (A) FLR3-1 cells and (B) R6FLR-N cells with a rabbit anti-BGT-1 polyclonal antibody or a mouse anti-AKR1C1 polyclonal antibody for 72 hours (n=3). "−" represents a group incubated without antibody, and normal mouse serum was used as a control of the anti-AKR1C1 antibody and normal rabbit serum was used as a control of the anti-BGT-1 antibody.

As a result, the RLU in FLR3-1 cells treated with the anti-BGT-1 antibody diluted at 1:100 declined to $6 \times 10^3$, in contrast to $1.2 \times 10^4$ in the same cells treated with normal mouse serum (FIG. 4A, $p<0.05$). The RLU in R6FLR-N cells treated with the anti-BGT-1 antibody diluted at 1:100 declined to $8 \times 10^3$, in contrast to $57 \times 10^3$ in the same cells treated with normal mouse serum (FIG. 4B, $p<0.05$). Thus, it was shown that the anti-BGT-1 antibody significantly inhibits the replication of HCV.

6. Cytotoxic Activity of Antibodies Against HCV-Replicating Cells

FLR3-1 cells and R6FLR-N cells were incubated with the rabbit anti-BGT-1 polyclonal antibody or mouse anti-AKR1C1 polyclonal antibody described above for 72 hours. After incubation, the $OD_{450/650}$ was measured by a chromogenic reaction at 37° C. for 1 hour using Cell Counting Kit-8 (DOJINDO) following the manufacturer's protocol. Normal rabbit serum was used as a control of the anti-BGT-1 antibody, and normal mouse serum was used as a control of the anti-AKR1C1 antibody. Each antibody was diluted at 1:100-1:10000 in 3% BSA/PBS. The experiment was performed in triplicate, and the average±S.D. was graphically shown. Statistical analysis was performed by Student's t-test.

As a result, the $OD_{450/650}$ in FLR3-1 cells treated with the anti-BGT-1 antibody diluted at 1:100 declined to 0.6, in contrast to about 1.3 in the cells treated with the same antibody diluted at 1:1000 (FIG. 5A, $p<0.05$). The $OD_{450/650}$ in R6FLR-N cells treated with the anti-BGT-1 antibody diluted at 1:100 declined to 0.3, in contrast to 1.2 in the cells treated with the same antibody diluted at 1:1000 (FIG. 5B, $p<0.05$). Thus, it was shown that the anti-BGT-1 antibody significantly injures the HCV-replicating cells.

7. Inhibitory Activity of Inhibitors Against HCV Replication

HCV-replicating cells were incubated with a BGT-1 inhibitor tiagabine or an AKR1C1 inhibitor flufenamic acid, and the inhibitory effect against HCV replication was evaluated by a luciferase assay. Tiagabine was dissolved in sterile distilled water at a final concentration of 1 mM, and flufenamic acid was dissolved in 1% EtOH at a final concentration of 1 μM-1 mM. The assay was performed after a reaction period of 24 hours in expectation of the rapid action of the inhibitors. The HCV-replicating cells used were FLR3-1, R6FLR-N (both genotype 1b) and JFH1 (genotype 2a: Kato et al., Gastroenterology, 2003, 125 (6):1808-17). The cells incubated in the medium alone were used as "controls". The experiment was performed in triplicate, and the average±S.D. was graphically shown. Statistical analysis was performed by Student's t-test.

Figure 7:
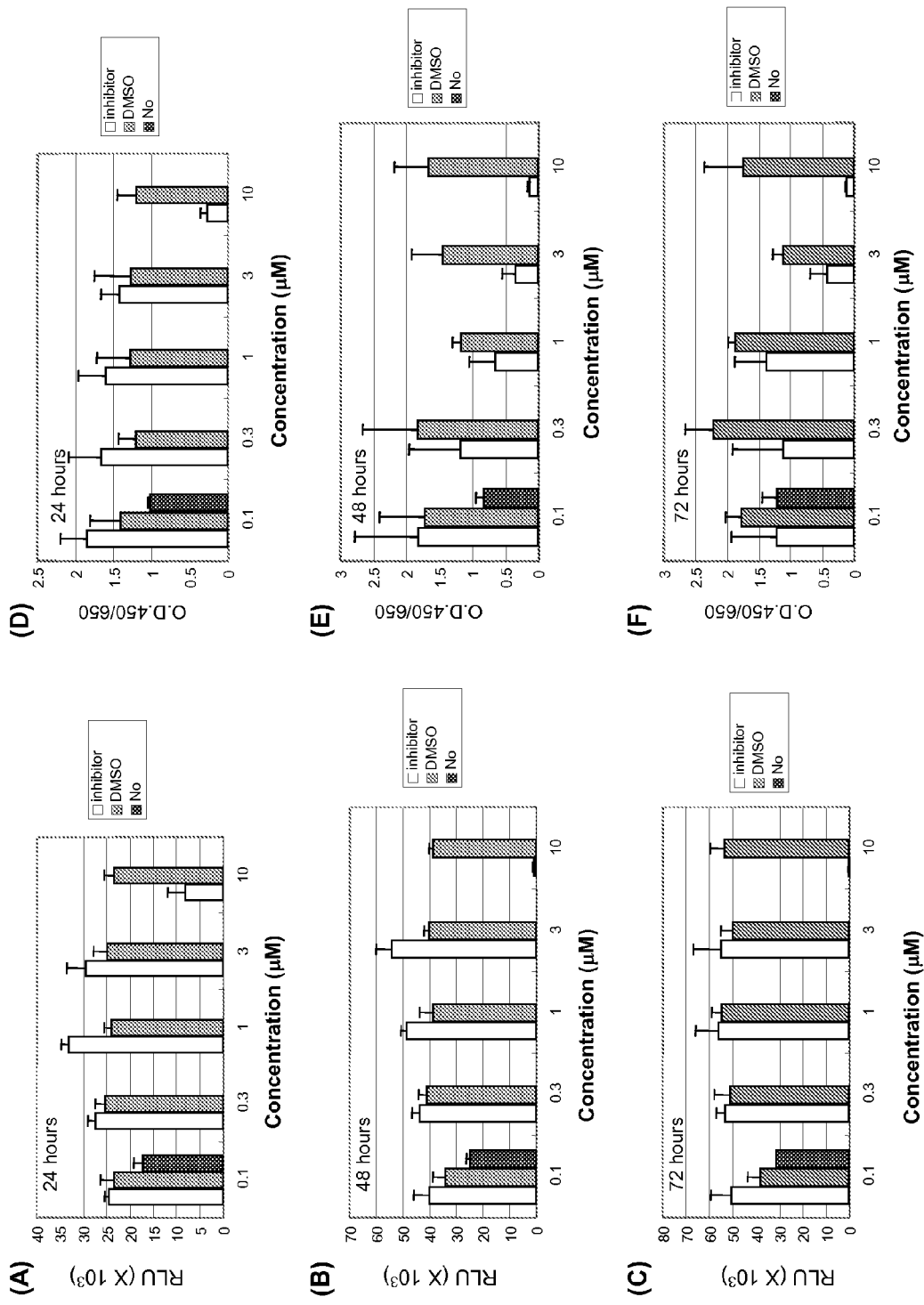
FIG. 7 represents graphs showing the results of an analysis of inhibitory activity against HCV replication (A-C) and cytotoxic activity against HCV-replicating cells (D-F) after incubation of R6FLR-N cells with a BGT-1 inhibitor NNC05-2090 at a final concentration of 0.1-10 μM for 24 hours (A and D), 48 hours (B and E), and 72 hours (C and F) (n=3). "DMSO" represents a vehicle group, and "No" represents a group incubated in culture medium alone.

R6FLR-N cells were also incubated with another BGT-1 inhibitor NNC05-2090 for 24-72 hours, and then analyzed by a luciferase assay in the same manner. NNC05-2090 was dissolved in DMSO at a final concentration of 0.1-10 μM (FIG. 7).

Figure 6:
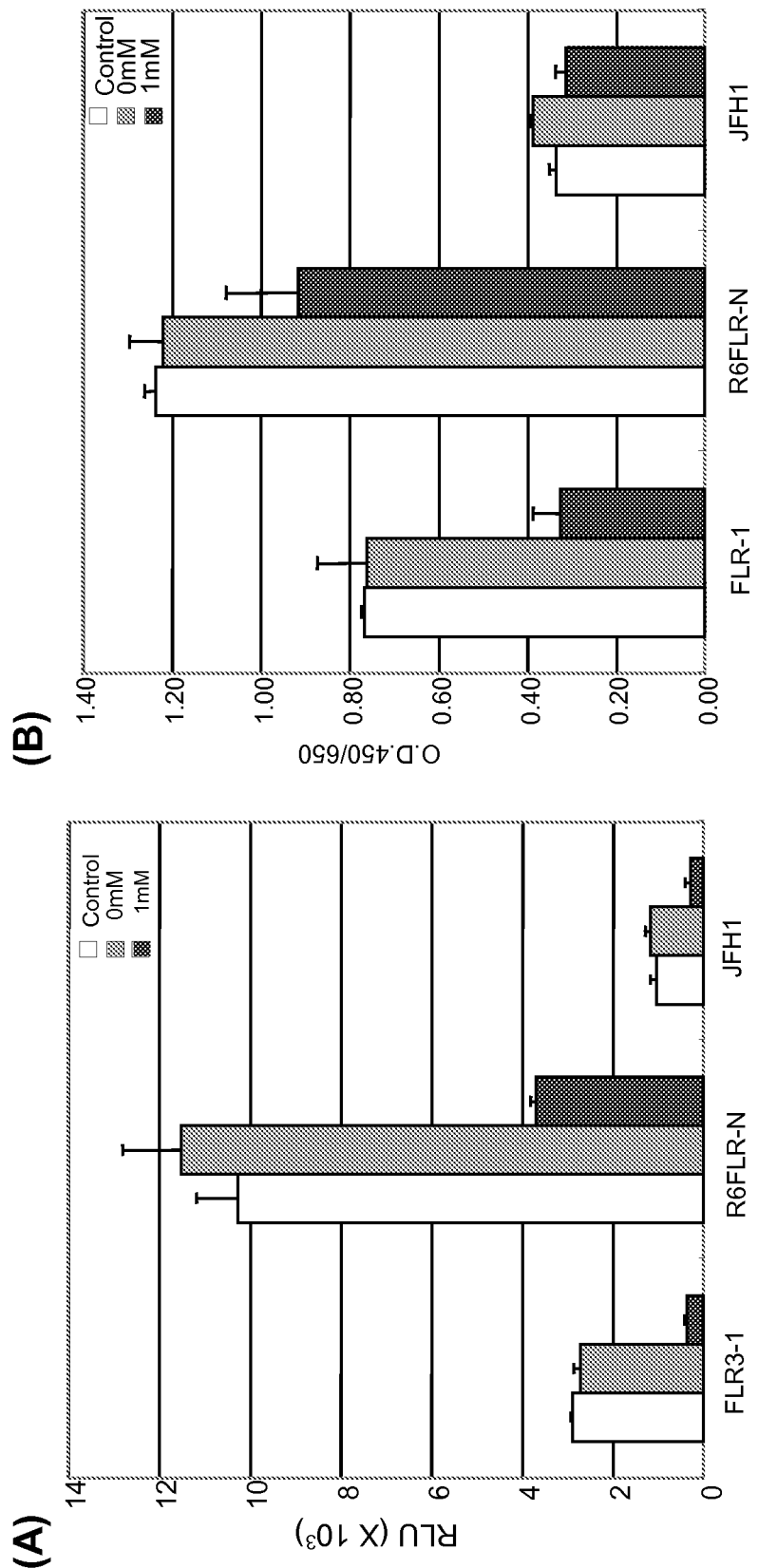
FIG. 6 represents graphs showing the results of an analysis of (A) inhibitory activity against HCV replication and (B) cytotoxic activity against HCV-replicating cells after incubation of FLR3-1, R6FLR-N, and JFH1 cells with a BGT-1 inhibitor tiagabine at a final concentration of 0 or 1 mM for 24 hours (n=3). "Control" represents a group incubated in culture medium alone.
Figure 8:
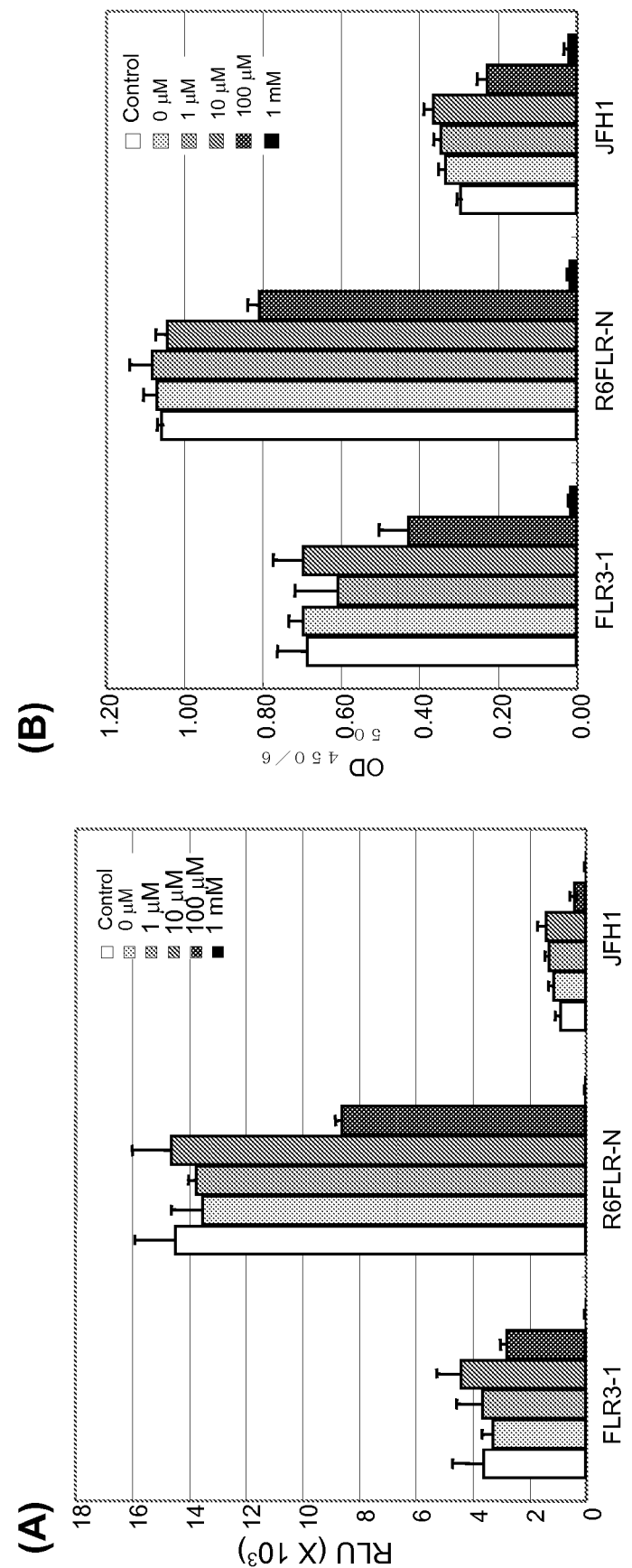
FIG. 8 represents graphs showing the results of an analysis of (A) inhibitory activity against HCV replication and (B) cytotoxic activity against HCV-replicating cells after incubation of FLR3-1, R6FLR-N, and JFH1 cells with an AKR1C1 inhibitor flufenamic acid at a final concentration of 1 mM for 24 hours (n=3). "Control" represents a group incubated in culture medium alone.

As a result, the RLU in the all types of HCV-replicating cells treated with tiagabine declined to 12.6±1.5 to 36±1.2% of the values of the control groups, thus showing a significant inhibitory activity against HCV replication (FIG. 6A, $p<0.05$). The RLU in the group treated with 10 μM NNC05-2090 declined to 30% vs. the vehicle group ("DMSO") even after incubation for 24 hours, thus showing a significant inhibitory activity against HCV replication (FIG. 7A, $p<0.05$). The RLU in the group treated with 100 μM flufenamic acid declined to 40±10 to 85.2±6% of the value of the 0 μM group, thus showing a significant inhibitory activity against HCV replication (FIG. 8A, $p<0.05$).

8. Cytotoxic Activity of Inhibitors Against HCV-Replicating Cells

In the same manner as described above, the cytotoxic activity of tiagabine (1 mM), NNC05-2090 (0.1-10 μM), and flufenamic acid (1 μM-1 mM) against HCV-replicating cells was evaluated by the WST assay. The experiment was performed in triplicate, and the average±S.D. was graphically shown. Statistical analysis was performed by Student's t-test.

As a result, tiagabine significantly injured HCV-replicating cells in only FLR3-1 cells (FIG. 6B, $p<0.05$). The OD value in the group treated with NNC05-2090 declined to about 23% of the vehicle group at 10 μM at 24 hours post-treatment (FIG. 7D, p<0.05), and to about 26% of the vehicle group at 3 μM at 48 hours post-treatment (FIG. 7E, p<0.05), thus showing a significant cytotoxic activity against HCV-replicating cells. The OD value in the all types of HCV-replicating cells treated with 100 μM flufenamic acid declined to 80% or less of the value of the 0 μM group, thus showing a significant cytotoxic activity (FIG. 8B, p<0.05).

INDUSTRIAL APPLICABILITY

The replication of HCV can be inhibited with high specificity by inhibiting BGT-1 and/or AKR1C1, and hepatitis C can be treated by specifically injuring HCV-infected cells. Especially, siRNAs of BGT-1 and AKR1C1 can inhibit HCV replication at lower concentrations than siRNAs of DHCR24, and siRNAs of BGT-1 are effective for the treatment of HCV infection because of their low cytotoxicity and the like.

The invention claimed is:

1. An siRNA of the BGT-1 gene consisting of the nucleotide (a), (b), or (c) below:
   (a) an nucleotide consisting of the nucleotide sequence 5'-CAACAAGAUGGAGUUUGUGCUGUCA-3' (SEQ ID NO: 1);
   (b) an nucleotide of 25-40 nucleotides in length including the nucleotide sequence 5'-CAACAAGAUGGAGUUUGUGCUGUCA-3' (SEQ ID NO: 1); or
   (c) an nucleotide capable of hybridizing an nucleotide consisting of a nucleotide sequence complementary to an nucleotide consisting of the nucleotide sequence of SEQ ID NO: 1 under stringent conditions and capable of inhibiting the replication of hepatitis C virus.

2. An siRNA of the AKR1C1 gene consisting of the nucleotide (a), (b), or (c) below:
   (a) an nucleotide consisting of the nucleotide sequence 5'-AAGUAAAGCUUUAGAGGCCACCAAA-3' (SEQ ID NO: 13);
   (b) an nucleotide of 25-40 nucleotides in length including the nucleotide sequence 5'-AAGUAAAGCUUUAGAGGCCACCAAA-3' (SEQ ID NO: 13); or
   (c) an nucleotide capable of hybridizing an nucleotide consisting of a nucleotide sequence complementary to an nucleotide consisting of the nucleotide sequence of SEQ ID NO: 13 under stringent conditions and capable of inhibiting the replication of hepatitis C virus.

3. A method for inhibiting the replication of hepatitis C virus comprising administering to a subject in need thereof an siRNA which inhibits BGT-1, and inhibiting hepatitis C virus by administration of the siRNA.

4. A method for inhibiting the replication of hepatitis C virus by administration to a subject in need thereof of an siRNA which inhibits BGT-1 and siRNA which inhibits AKR1C1.

5. A method for inhibiting the replication of hepatitis C virus comprising administering to a subject in need thereof an siRNA which inhibits AKR1C1, and inhibiting hepatitis C virus by the siRNA.

6. A method for inhibiting the replication of hepatitis C virus comprising (a) detecting hepatitis C virus and (b) administering to a subject in need thereof an inhibitor of BGT-1 and/or AKR1C1, and (c) inhibiting hepatitis C virus by administration of the inhibitor of BGT-1 and/or AKR1C1.

* * * * *